United States Patent [19]

Harandi et al.

[11] Patent Number: 5,011,506
[45] Date of Patent: Apr. 30, 1991

[54] INTEGRATED ETHERIFICATION AND ALKENE HYDRATION PROCESS

[75] Inventors: Mohsen N. Harandi, Lawrenceville; Hartley Owen, Belle Mead, both of N.J.

[73] Assignee: Mobil Oil Corporation, Fairfax, Va.

[21] Appl. No.: 414,861

[22] Filed: Sep. 29, 1989

[51] Int. Cl.$^5$ .............................................. C10L 1/18
[52] U.S. Cl. .................................. 44/447; 568/697; 568/895; 568/899
[58] Field of Search ............... 44/56, 53, 77; 568/697, 568/698, 699; 585/310, 318, 639, 654, 655, 737, 738

[56] References Cited

U.S. PATENT DOCUMENTS

| | | | |
|---|---|---|---|
| 4,334,890 | 6/1982 | Kochar et al. | 44/53 |
| 4,393,250 | 7/1983 | Gottlieb et al. | 568/697 |
| 4,423,251 | 12/1983 | Pujado et al. | 568/697 |
| 4,544,776 | 10/1985 | Osterburg et al. | 568/697 |
| 4,647,703 | 3/1987 | Torck et al. | 568/697 |
| 4,664,755 | 5/1987 | Torck et al. | 44/56 |
| 4,827,045 | 5/1989 | Harandi et al. | 568/697 |
| 4,857,664 | 8/1989 | Huang et al. | 568/695 |

Primary Examiner—Margaret B. Medley
Attorney, Agent, or Firm—Alexander J. McKillop; Charles J. Speciale; L. G. Wise

[57] ABSTRACT

A method is disclosed combining the process for the hydration or etherification of light linear olefins, such as the production of diisopropyl ether (DIPE), with the process for the etherification of $C_4+$ or $C_4$ hydrocarbons containing isobutylene to produce alkyl tertiary butyl ether or ether-rich gasoline in a manner which effectively dewaters alkanol using the iso-olefin hydrocarbon feedstream as extractant. The combined process leads to the production of isopropyl tert-alkyl ethers. In the integrated process the high octane ethers produced may include methyl tert-butyl ether, methyl tert-amyl ether, isopropyl tert-butyl ether and diisopropyl ether. The process also results in the production of a gasoline stream rich in high octane ethers.

12 Claims, 1 Drawing Sheet

INTEGRATED ETHERIFICATION AND ALKENE HYDRATION PROCESS

This invention relates to a method for combining the processes for the production of high octane ethers associated with the etherification of iso-olefins and hydration of linear olefins. More particularly, the invention relates to a process integration wherein wet alkanol from linear olefin hydration is dewatered using the hydrocarbon feedstream to an alkyl tert-alkyl ether etherification zone and combined therewith for tert-alkyl ether production.

BACKGROUND OF THE INVENTION

Lower molecular weight alcohols and ethers such as isopropanol (IPA) and diisopropyl ether (DIPE) are in the gasoline boiling range and are known to have high blending octane numbers. In addition, by-product propylene from which IPA and DIPE can be made is usually available in a fuels refinery. One important focus of research in the petroleum industry is processes to produce high octane gasolines blended with lower aliphatic alkyl ethers as octane boosters and supplementary fuels. Generally, it is known that asymmetrical $C_5$–$C_7$ alkyl tertiary alkyl ethers and diisopropyl ether (DIPE) are particularly useful as octane improvers for liquid fuels, especially gasoline. MTBE, ethyl tert-butyl ether (ETBE), isopropyl tert-butyl ether (IPTBE) and TAME are known to be high octane ethers. The article by J. D. Chase, et al., *Oil and Gas Journal*, Apr. 9, 1979, discusses the advantages one can achieve by using such materials to enhance gasoline octane. The octane blending number of MTBE when 10% is added to a base fuel (R+O=91) is about 120. For a fuel with a low motor rating (M+O=83) octane, the blending value of MTBE at the 10% level is about 103. On the other hand, for an (R+O) of 95 octane fuel, the blending value of 10% MTBE is about 114. Increasing demand for high octane gasolines blended with high octane ethers as octane boosters and supplementary fuels has created a significant demand for these ethers, especially MTBE and TAME. Improvements to the processes related to the production of these ethers are matters of high importance and substantial challenge to research workers in the petroleum refining arts.

The catalytic hydration of olefins to provide alcohols and ethers is a well-established art and is of significant commercial importance. Representative olefin hydration processes are disclosed in U.S. Pat. Nos. 2,262,913; 3,798,097; 3,198,752; 3,810,848; 3,989,762, among others.

The production of ether from secondary alcohols such as isopropanol and light olefins is also known. As disclosed in U.S. Pat. No. 4,182,914, DIPE is produced from IPA and propylene in a series of operations employing a strongly acidic cation exchange resin as catalyst.

It is well known that isobutylene may be reacted with methanol over an acidic catalyst to provide methyl tertiary butyl ether (MTBE) and isoamylenes may be reacted with methanol over an acidic catalyst to produce tertiary amyl methyl ether (TAME). The reaction is a useful preparation for these valuable gasoline octane enhancers and is typical of the reaction of the addition of lower alkanol to the more reactive tertiary alkenes, or iso-olefins, of the type $R_2C=CH_2$ under mild conditions to form the corresponding tertiary alkyl ethers.

The feedstock for the etherification reaction may be taken from a variety of refinery process streams such as the unsaturated gas plant of a fluidized bed catalytic cracking operation containing mixed light olefins, preferably rich in isobutylene. Light olefins such as propylene and butenes other than isobutylene in the feedstock are essentially unreactive toward alcohols under the mild, acid catalyzed etherification reaction conditions employed to produce lower alkyl tertiary butyl ether.

The crude methanol source for methanol for the MTBE reaction typically contains a significant amount of water. For the etherification reaction to proceed effectively it is important that water in the crude methanol be reduced. In the DIPE process, the reaction of water with propylene to produce DIPE also produces a by-product stream consisting of isopropanol and water. To maintain high conversion it is required in the prior art that this stream be recycled to the DIPE unit.

It is an object of the present invention to provide an integrated process for the manufacture of alkyl tertiary alkyl ethers using dewatered alkanol byproduct from linear olefins hydration as feedstream to iso-olefins etherification.

Another object of the present invention is to provide a process for the manufacture of methyl or isopropyl tert-alkyl ether and diisopropyl ether in a design integrated with DIPE production.

It is another object of this invention to provide an integrated MTBE and DIPE process which additionally produces isopropyl tert-butyl ether.

Yet another object of the present invention is to provide an integrated process for the manufacture of high octane ethers containing methyl tert-alkyl ethers, DIPE and including high octane gasoline.

SUMMARY OF THE INVENTION

A method has been discovered to combine processes for the hydration of light olefins and production of ethers such as DIPE with the process for the alkanol etherification of $C_4+$ iso-olefinic hydrocarbons to produce ether-rich gasoline in a manner which effectively dewaters alkanol feedstock using the $C_4+$ hydrocarbon feedstream as extractant. The combined process leads to the production of ethers such as methyl tert-butyl ether, methyl tert-amyl ether and isopropyl tert-butyl ether. The process also results in the production of a gasoline stream rich in high octane ethers. In the integrated process the light, linear olefin hydration product, or by-product, comprising $C_2$–$C_4$ alkanol is dewatered with $C_4+$, or $C_4$, iso-olefin-rich feedstock and converted to tert-ethers. A wet methanol feedstream may be included in the integrated dewatering step to produce MTBE and TAME.

More particularly, an integrated process for the production of high octane ethers has been discovered which comprises extracting an aqueous alkanol effluent stream from a light olefins hydration zone with a hydrocarbon feedstream to a lower alkyl tert-alkyl ether production zone. The feedstream to the tert-alkyl etherification zone contains isobutylene and/or isoamylene. The aqueous raffinate stream is separated after extraction and contains some alkanol and an organic extract stream comprising the tert-alkyl ether hydrocarbon feedstream which contains a major portion of dewatered alkanol.

The organic stream is passed to the tert-alkyl ether production zone in contact with acidic iso-olefin etherification catalyst under etherification conditions to produce an etherification effluent stream comprising tert-alkyl ethers of alkanol and unreacted hydrocarbons.

The aqueous raffinate stream, a fresh water feedstream and light, linear olefin hydrocarbon feedstream can be passed to an ether production zone in contact with acidic olefin hydration and etherification catalyst under olefin hydration and etherification conditions to produce linear ethers and alkanol such as diisopropyl ether, dibutyl ether, isopropanol, 1-butanol, 2-butanol and the like.

DESCRIPTION OF THE FIGURE

Figure is a schematic diagram of the process of the present invention.

DETAILED DESCRIPTION OF THE INVENTION

Figure 1:
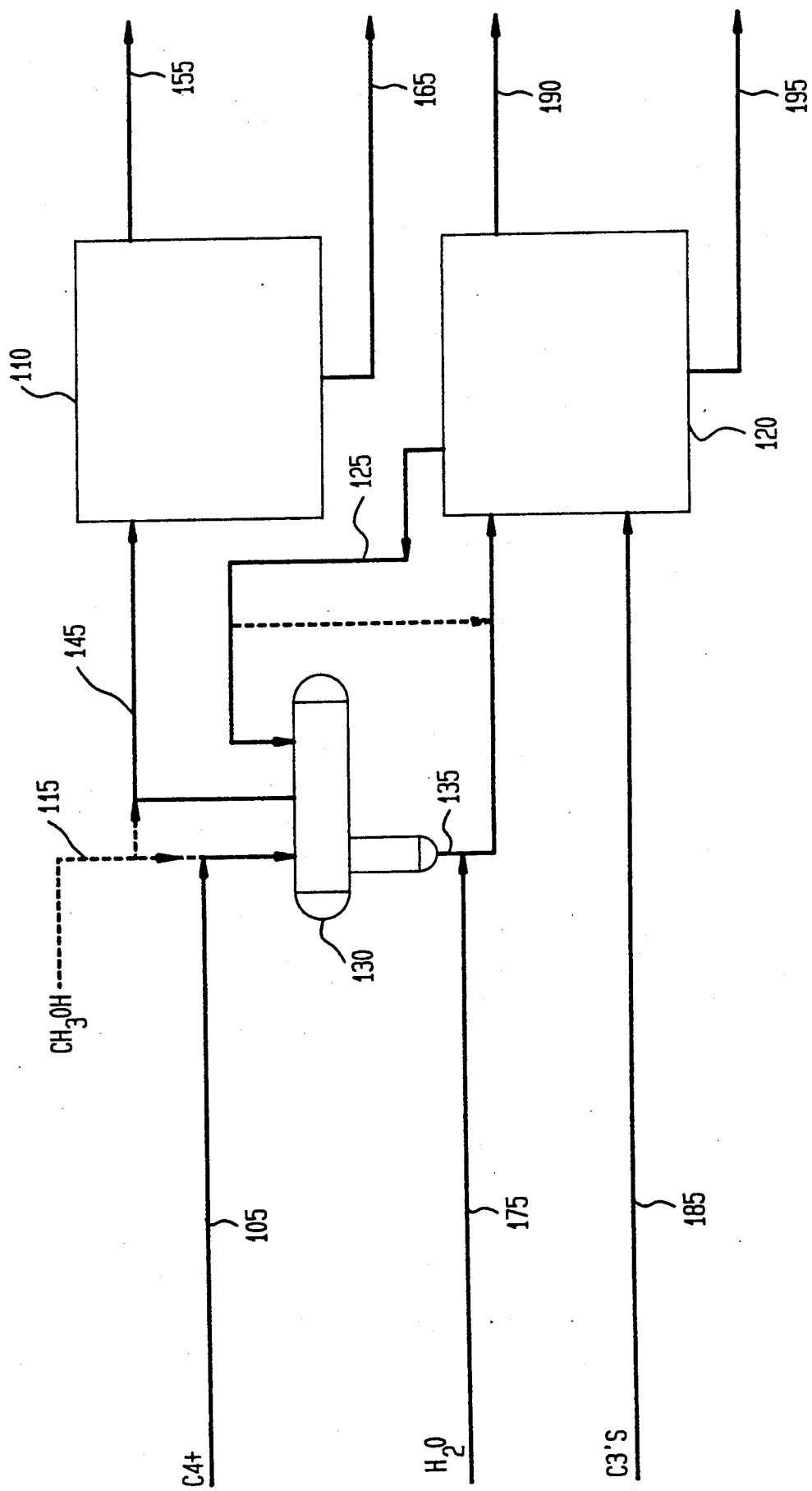

Referring to the figure, a preferred embodiment of the process of the instant invention is illustrated in a schematic flow diagram. The diagram shows an etherification unit 110 for the conversion of $C_1$-$C_4$ alkanol to lower alkyl tert-alkyl ethers; and olefins hydration and/or etherification unit 120 for the etherification and/or hydration of $C_3$ hydrocarbons containing propylene to produce high octane diisopropyl ether, with isopropanol as by-product. These units, 110 and 120, are integrated into a combined process through separator 130.

In the process of this invention a $C_4+$ hydrocarbon feedstock, rich in iso-olefins and particularly isobutylene and isoamylene, is employed as feedstock and mixed through conduit 105 with a $C_1$-$C_4$ alkanol feedstream 115, preferably wet methanol. In the invention a $C_4$ feedstream containing isobutylene may also be used rather than $C_4+$ feedstream. Also, while wet methanol is a preferred alkanol, ethanol, isopropanol, 1-butanol and 2-butanol may also be used as the alkanol feedstream, individually or in combination. The mixture of $C_4+$ hydrocarbon feedstock and wet methanol is passed to a separator 130 where it comes in contact with a by-product stream 125 comprising aqueous isopropanol from the DIPE unit. In the separator isopropanol and methanol are extracted into the hydrocarbon feedstream and an aqueous raffinate stream 135 is separated which contains some methanol and isopropanol. The major portion of methanol and isopropanol is separated from the separator/extractor unit 130 as an organic stream 145. In this process the methanol feedstream as well as the aqueous isopropanol DIPE by-product stream are effectively dewatered. The organic stream 145 is passed to the iso-olefins unit 110 where etherification is carried out in contact with acidic catalyst. The iso-olefins etherification effluent stream is separated, typically by fractionation and/or extraction, to produce an ether-rich gasoline stream 155 and an unreacted $C_4$ stream 165. When the alkanol is methanol the ether-rich gasoline contains MTBE, TAME, isopropyl tert-butyl ether, isopropyl tert-amyl ether. When the hydrocarbon feedstream is $C_4$, the hydrocarbon effluent stream 155 comprises MTBE and isopropyl tert-butyl ether.

From separator 130 the aqueous raffinate 135 is combined with water 175 and introduced into the DIPE etherification zone in conjunction with $C_3$'s hydrocarbon feedstream 185. Hydration and etherification of $C_3$'s is carried out in contact with acidic catalyst. The product of the hydration and etherification, after separation, is diisopropyl ether stream 190 and unreacted $C_3$ hydrocarbon stream 195. To the extent that a minor portion of alkanol such as methanol is contained in the raffinate from separator 130 a minor portion of methyl isopropyl ether may also be produced in the DIPE etherification unit. The separation also produces the by-product aqueous isopropanol stream 125 which, conventionally, is recycled to the DIPE unit, but in the instant invention is integrated with the iso-olefins etherification process as described. Separation of the effluent from the DIPE unit 120 can be achieved by a variety of means known to those skilled in the art.

In the foregoing description of a preferred embodiment of the instant invention certain variations of the invention will be obvious to those skilled in the art. In particular, the alkanol feedstream 115 may be eliminated and the dewatered alkanol from the hydration and/or etherification step 190 used as the sole alkanol feed to etherification zone 110, after extraction with the iso-olefin etherification feedstream 105. In the foregoing recitation, implementation of this variation of the process produces isopropyl tert-butyl ether and, when the feedstream is $C_4+$ iso-olefins, isopropyl tert-amyl ether. Optionally, dry methanol may be passed directly to etherification zone 110. Also, it is apparent that the hydration and/or etherification step 190 can, as well, comprise hydration and/or etherification of other linear olefins such as butene since these processes are well known in the art. Conditions can be adjusted to control the linear olefins hydration step to produce predominantly alkanol as the product to be subjected to dewatering in separator 130.

Lower alkyl in the present invention refers to $C_1$-$C_4$ alkyl derived from etherification using lower alkanol such as methanol, ethanol, 1-propanol, isopropanol, 2-butanol and 1-butanol. Tertiary alkyl refers to $C_4$-$C_5$ tertiary alkyl groups derived from the etherification of iso-olefins such as isobutene and isoamylene. Light, linear olefins include ethene, propene, butene-1 and butene-2.

Methanol may be readily obtained from coal by gasification to synthesis gas and conversion of the synthesis gas to methanol by well-established industrial processes. As an alternative, the methanol may be obtained from natural gas by other conventional processes, such as steam reforming or partial oxidation to make the intermediate syngas. Crude methanol from such processes usually contains a significant amount of water, usually in the range of 4 to 20 wt%. The etherification catalyst employed is preferably an ion exchange resin in the hydrogen form; however, any suitable acidic catalyst may be employed. Varying degrees of success are obtained with acidic solid catalysts; such as, sulfonic acid resins, phosphoric acid modified kieselguhr, silica alumina and acid zeolites such as zeolite beta and ZSM-5. Typical hydrocarbon feedstock materials for iso-olefin etherification reactions include $C_4+$ olefinic streams, such as FCC light naphtha and $C_4$ butenes rich in isobutene. These aliphatic streams are produced in petroleum refineries by catalytic cracking of gas oil or the like.

The reaction of methanol with isobutylene and isoamylenes at moderate conditions with a resin catalyst is known technology, as provided by R. W. Reynolds, et al., *The Oil and Gas Journal*, June 16, 1975, and S. Pecci and T. Floris, *Hydrocarbon Processing*, December 1977. An article entitled "MTBE and TAME - A Good Octane Boosting Combo", by J. D. Chase, et al., *The Oil and Gas Journal*, Apr. 9, 1979, pages 149–152, discusses the technology. A preferred catalyst is a bifunctional ion exchange resin which etherifies and isomerizes the reactant streams. A typical acid catalyst is Amberlyst 15 sulfonic acid resin, a product of Rohm and Haas Corporation.

MTBE is known to be a high octane ether. The article by J. D. Chase, et al., *Oil and Gas Journal*, Apr. 9, 1979, discusses the advantages one can achieve by using these materials to enhance gasoline octane. The octane blending number of MTBE when 10% is added to a base fuel (R+O=91) is about 120. For a fuel with a low motor rating (M+O=83) octane, the blending value of MTBE at the 10% level is about 103. On the other hand, for an (R+O) of 95 octane fuel, the blending value of 10% MTBE is about 114.

Processes for producing and recovering MTBE and other methyl tertiary alkyl ethers from iso-olefins are known to those skilled in the art, such as disclosed in U.S. Pat. Nos. 4,544,776 (Osterburg, et al.) and 4,603,225 (Colaianne, et al.). In the prior art various suitable extraction and distillation techniques are known for recovering ether and hydrocarbon streams from etherification effluent.

In the present invention methanol, or other lower alkanol, may be present in the iso-olefin etherification zone in a stoichiometric excess amount. The alkanol feedstream may be up to 100% mole percent in excess. In the absence of alkanol feedstream the sole alkanol reactant to the isoolefin etherification zone is isopropanol and the reaction products are tertiary alkyl ethers of isopropanol, i.e., isopropyl tertiary butyl ether and isopropyl tertiary amyl ether.

The operating conditions of the olefin hydration and etherification process to produce DIPE include a temperature of from about 60° to 450° C., preferably from about 90° to about 220° C. and most preferably from about 120° to about 200° C., a pressure of from about 100 to about 3500 psi, preferably from about 500 to about 2000 psi, a water to olefin mole ratio of from about 0.1 to about 30, preferably from about 0.2 to about 15 and most preferably from about 0.3 to about 3.

The olefin hydration and etherification process combined in this invention can be carried out under dense phase, liquid phase, vapor phase or mixed vapor liquid phase conditions in batch or continuous manner using a stirred tank reactor or fixed bed flow reactor, e.g., trickle-bed, liquid-up-flow, liquid-down-flow, counter-current, co-current, etc. Reaction times of from about 20 minutes to about 20 hours when operating in batch and an olefin WHSV of from about 0.1 to about 20, preferably about 0.1-2, when operating continuously are suitable. A portion of unreacted olefin may be recovered and recycled to the reactor. For DIPE, the DIPE per pass selectivity of isopropanol in this invention may be 10-99%, preferably about 50%.

The catalyst employed in the olefin hydration and etherification operations which are integrated with isoolefin etherification operations is any acidic catalyst, although shape-selective acidic zeolite is preferred. In general, the useful catalysts embrace two categories of zeolite, namely, the intermediate pore size variety as represented, for example, by ZSM-5, which possess a Constraint Index of greater than about 2 and the large pore variety as represented, for example, by zeolites Y, Beta and ZSM-12, which possess a Constraint index no greater than about 2. Preferred catalysts include Zeolite Beta, Zeolite Y, ZSM-12, ZSM-5 and ZSM-35. Both varieties of zeolites will possess a framework silica-to-alumina ratio of greater than about 7. In addition, acid resin catalysts are useful, such as Amberlyst 15 (Rohm & Haas) and other sulfonated vinyl aromatic resins.

The method by which Constraint Index is determined is described fully in U.S. Pat. No. 4,016,218, to which reference is made for details of the method. Constraint Index (CI) values for some zeolites which can be used in the process of this invention are described in the following table together with the temperature at which the test was made:

| Zeolite | Constraint Index (At Test Temperature, °C.) |
| --- | --- |
| ZSM-4 | 0.5 (316) |
| ZSM-5 | 6-8.3 (371-316) |
| ZSM-11 | 5-8.7 (371-316) |
| ZSM-12 | 2.3 (316) |
| ZSM-20 | 0.5 (371) |
| ZSM-35 | 4.5 (454) |
| ZSM-48 | 3.5 (538) |
| ZSM-50 | 2.1 (427) |
| TMA Offretite | 3.7 (316) |
| TEA Mordenite | 0.4 (316) |
| Clinoptilolite | 3.4 (510) |
| Mordenite | 0.5 (316) |
| REY | 0.4 (316) |
| Amorphous Silica-Alumina | 0.6 (538) |
| Dealuminized Y | 0.5 (510) |
| Zeolite Beta | 0.6-2.0 (316-399) |

ZSM-5 is more particularly described in U.S. Reissue Pat. No. 28,341 (of original U.S. Pat. No. 3,702,886), the entire contents of which are incorporated herein by reference.

ZSM-11 is more particularly described in U.S. Pat. No. 3,709,979, the entire contents of which are incorporated herein by reference.

ZSM-23 is more particularly described in U.S. Pat. No. 4,076,842, the entire contents of which are incorporated herein by reference.

ZSM-35 is more particularly described in U.S. Pat. No. 4,016,245, the entire contents of which are incorporated herein by reference.

ZSM-38 is more particularly described in U.S. Pat. No. 4,046,859, the entire contents of which are incorporated herein by reference. Although ZSM-38 possesses a Constraint Index of 2.0, it is often classified with the intermediate pore size zeolites and will therefore be regarded a such for purposes of this invention.

The large pore zeolites which are useful a catalysts in the process of this invention, i.e., those zeolites having a Constraint Index of no greater than about 2, are well known to the art. Representative of these zeolites are zeolite Beta, zeolite X, zeolite L, zeolite Y, ultrastable zeolite Y (USY), dealuminized Y (Deal Y), rare earth-exchanged zeolite Y (REY), rare earth-exchanged dealuminized Y (RE Deal Y), mordenite, ZSM-3, ZSM-4, ZSM-12, ZSM-20, and ZSM-50 and mixtures of any of the foregoing. Although zeolite Beta has a Constraint Index of about 2 or less, it should be noted that this zeolite does not behave exactly like other large pore zeolites. However, zeolite Beta does satisfy the requirements for a catalyst of the present invention.

Zeolite Beta is described in U.S. Reissue Pat. No. 28,341 (of original U.S. Pat. No. 3,308,069), to which reference is made for details of this catalyst.

Zeolite X is described in U.S. Pat. No. 2,882,244, to which reference is made for the details of this catalyst.

Zeolite L is described in U.S. Pat. No. 3,216,789, to which reference is made for the details of this catalyst.

Zeolite Y is described in U.S. Pat. No. 3,130,007, to which reference is made for details of this catalyst.

Low sodium ultrastable zeolite Y (USY) is described in U.S. Pat. Nos. 3,293,192; 3,354,077; 3,375,065; 3,402,996; 3,449,070; and 3,595,611, to which reference is made for details of this catalyst.

Dealuminized zeolite Y (Deal Y) can be prepared by the method found in U.S. Pat. No. 3,442,795, to which reference is made for details of this catalyst.

Zeolite ZSM-3 is described in U.S. Pat. No. 3,415,736, to which reference is made for details of this catalyst.

Zeolite ZSM-4 is described in U.S. Pat. No. 3,923,639, to which reference is made for details of this catalyst.

Zeolite ZSM-12 is described in U.S. Pat. No. 3,832,449, to which reference is made for the details of this catalyst.

Zeolite ZSM-20 is described in U.S. Pat. No. 3,972,983, to which reference is made for the details of this catalyst.

Zeolite ZSM-50 is described in U.S. Pat. No. 4,640,829, to which reference is made for details of this catalyst.

While the invention has been described by specific examples and embodiments, there is no intent to limit the inventive concept except as set forth in the following claims.

What is claimed is:

1. An integrated process for the production of high octane ethers, comprising:
   extracting a methanol feedstream containing water and an aqueous isopropanol by-product effluent stream from a diisopropyl ether production zone with a hydrocarbon feedstream to a methyl tert-alkyl ether production zone, said feedstream containing isobutylene and/or isoamylene;
   separating an aqueous raffinate stream after extraction containing a minor portion of both said isopropanol and methanol and an organic extract stream comprising said hydrocarbon feedstream containing a major portion of both dewatered methanol and dewatered isopropanol;
   passing said organic stream to said tert-alkyl ether production zone in contact with acidic iso-olefin etherification catalyst under etherification conditions to produce an etherification effluent stream comprising tert-alkyl ethers of methanol and isopropanol, methyl isopropyl ether and unreacted hydrocarbons;
   passing said aqueous raffinate stream, a fresh water feedstream and $C_3$ hydrocarbon feedstream containing propene to said diisopropyl ether production zone in contact with acidic olefin hydration and etherification catalyst under olefin hydration and etherification conditions to produce effluent streams from said diisopropyl ether production zone comprising diisopropyl ether stream, methyl isopropyl ether, said aqueous isopropanol by-product stream and unreacted $C_3$ hydrocarbons stream.

2. The process of claim 1, wherein said tert-alkyl ethers of methanol and isopropanol comprise methyl tert-butyl ether, isopropyl tert-butyl ether, methyl tert-amyl ether and isopropyl tert-amyl ether.

3. The process of claim 1 wherein said hydrocarbon feedstream comprises $C_4+$ hydrocarbons.

4. The process of claim 3 further comprising separating said tert-alkyl ether production zone effluent stream to produce a stream comprising high octane ether rich gasoline and a stream comprising unreacted $C_4$ hydrocarbons.

5. The process of claim 1 wherein said hydrocarbon feedstream to methyl tert-alkyl ether production zone comprises $C_4$ hydrocarbons rich in isobutene and said ethers comprise methyl tert-butyl ether and isopropyl tert-butyl ether.

6. The process of claim 1 wherein said methanol feedstream contains between about 0.1% and 10% water.

7. The process of claim 1 wherein said acidic olefin hydration and etherification catalyst and said acidic isoolefin etherification catalyst is taken from the group consisting essentially of acidic zeolites and acidic resins.

8. The process of claim 1 wherein said acidic olefin hydration and etherification catalyst and said acidic isoolefin etherification catalyst is taken from the group consisting essentially of ZSM-5, zeolite Beta and sulfonated polystyrene resins.

9. An integrated process for the production of methyl tert-butyl ether and diisopropyl ether, comprising:
   extracting a methanol feedstream containing water and an aqueous isopropanol by-product effluent stream from a diisopropyl ether production zone with a $C_4$ hydrocarbon feedstream to a methyl tert-butyl ether production zone, said feedstream containing isobutylene;
   separating an aqueous raffinate stream after extraction containing a minor portion of both said isopropanol and hydrocarbon feedstream containing a major portion of both dewatered methanol and dewatered isopropanol;
   passing said organic stream to said tert-butyl ether production zone in contact with acidic iso-olefin etherification catalyst under etherification conditions to produce an etherification effluent stream comprising methyl tert-butyl ether, isopropyl tert-butyl ether, methyl isopropyl ether and unreacted $C_4$ hydrocarbons;
   passing said aqueous raffinate stream, a fresh water feedstream and $C_3$ hydrocarbon feedstream containing propene to said diisopropyl ether production zone in contact with acidic olefin hydration and etherification catalyst under olefin hydration and etherification conditions to produce effluent streams from said diisopropyl ether production zone comprising diisopropyl ether stream, methyl isopropyl ether, said aqueous isopropanol by-product stream and unreacted $C_3$ hydrocarbons stream.

10. The process of claim 9 wherein said methanol feedstream contains between about 0.1% and 10% water.

11. The process of claim 9 wherein said acidic olefin hydration and etherification catalyst and said acidic isoolefin etherification catalyst is taken from the group consisting essentially of acidic zeolites and acidic resins.

12. The process of claim 9 wherein said acidic olefin hydration and etherification catalyst and said acidic isoolefin etherification catalyst is taken from the group consisting essentially of ZSM-5, zeolite Beta and sulfonated polystyrene resins.

* * * * *